United States Patent [19]

Butter et al.

[11] 4,070,411

[45] Jan. 24, 1978

[54] CONVERSION OF LOWER OLEFINS TO ISOBUTANE

[75] Inventors: Stephen A. Butter, East Windsor; Warren W. Kaeding, Westfield, both of N.J.

[73] Assignee: Mobil Oil Corporation, New York, N.Y.

[21] Appl. No.: 730,490

[22] Filed: Oct. 7, 1976

Related U.S. Application Data

[63] Continuation of Ser. No. 562,278, March 26, 1975, abandoned.

[51] Int. Cl.$^2$ ............................................. C07C 9/12
[52] U.S. Cl. .......................... 260/676 R; 260/683.43
[58] Field of Search .......... 260/676 R, 683.65, 683.43, 260/683 D; 252/455 Z; 208/46, 71

[56] References Cited

U.S. PATENT DOCUMENTS

| | | | |
|---|---|---|---|
| 3,709,979 | 1/1973 | Chu | 208/111 |
| 3,760,024 | 9/1973 | Cattanach | 260/673 |
| 3,827,968 | 8/1974 | Givens et al. | 260/673.5 |

*Primary Examiner*—Herbert Levine
*Attorney, Agent, or Firm*—Charles A. Huggett; Michael G. Gilman; Alverna M. Paulan

[57] ABSTRACT

The conversion of lower olefins, such as ethylene or propylene, in effective contact with HZSM-11 catalyst at elevated temperatures to produce a product having a significant isobutane content.

4 Claims, No Drawings

CONVERSION OF LOWER OLEFINS TO ISOBUTANE

This application is a continuation of application Ser. No. 562,278, filed Mar. 26, 1975 now abandoned.

This invention relates to the conversion of unsaturated hydrocarbons. It more particularly relates to the conversion of lower olefins to isoparaffins.

It is known in the art to convert lower olefins to various oligomers thereof, including higher, normally liquid olefins. Thus, in U.S. Pat. No. 3,827,968, there is disclosed a technique of oligomerizing lower olefins to normally liquid olefins and then aromatizing these normally liquid olefins over a ZSM-5 type catalyst.

In U.S. Pat. No. 3,760,024, there is disclosed a process for directly converting lower olefins, such as ethylene, propylene or butene over a ZSM-type zeolite to gasoline boiling range product which is highly aromatic.

ZSM-5 zeolites are typical of a new class of zeolite catalysts which have very high silica to alumina ratios of at least about 15 and are shape selective for monomethyl substituted paraffins and smaller diameter organic compounds.

U.S. Pat. No. 3,709,979, discloses and claims as a new composition of matter, a crystalline aluminosilicate zeolite, namely ZSM-11. In Column 7 of this reference, this material is stated to be useful for hydrocracking, catalytic cracking, reforming, paraffin isomerization, olefin isomerization, hydrogenation and desulfurization reactions. In each of these uses, except for the catalytic cracking use, the U.S. Pat. No. 3,709,979 patent suggests the incorporation of a hydrogenation or hydrogenation/dehydrogenation function along with the zeolite.

It is not uncommon for refinery operations in certain modes and with certain charge stocks to have an imbalance whereby they have more light olefin product than they can use and have less isobutane than required to support the alkylation of all of the olefin available. Under these circumstances, refiners often have to go into the open market to purchase merchant isobutane in order to make alkylate which is a very desirable component of high octane gasoline. It is, therefore, obviously desirable for refiners to have available to them a process for converting relatively less valuable excess light olefin components to relatively more valuable isobutane suitable for subsequent use in alkylation processes.

It is, therefore, an object of this invention to provide such a process for converting light olefins to a product having high proportions of isobutane.

Other and additional objectives of this invention will become apparent from a consideration of the subject application including the claims hereof.

In accord with and fulfilling these objectives, one aspect of this invention resides in the conversion of lower olefins, preferably ethylene and/or propylene, to produce products having a high proportion of isobutane, preferably a product in which the ratio of isobutane to normal butane is at least about 6. This conversion is accomplished by contacting such lower olefins at relatively high temperatures of about 300° to 500° C with a ZSM-11 crystalline aluminosilicate zeolite catalyst at space velocities of about 0.5 to 100 WHSV. It is preferred to operate at lower temperatures up to about 400° C. The process can be carried out in the presence or absence of added hydrogen, preferably in the absence of added hydrogen, and is suitably carried out with a HZSM-11 catalyst alone or in a suitable matrix. Appropriate matrices for ZSM-11 include alumina, silica-alumina or silica. Where a matrix is used, the ZSM-11 suitably constitutes about 25 to 75 wt.% of the total solid catalyst particle. The conversion can be carried out in a fixed bed or fluid bed arrangement in a upflow or downflow reactor as is conventional reactor design techniques in the petroleum arts.

The following examples will illustrate the practice of this invention as well as the prior art background against which this invention has been made.

In each of the following runs ethylene, with or without nitrogen diluent as set forth, was contacted with the indicated zeolite catalyst at the indicated reaction conditions to produce the recited product distribution. Runs 1 to 7 show conversion of ethylene over HZSM-5 zeolite over a range of temperatures from 300° to 600° C in which the product produced has a consistent isobutane to normal butane ratio less than 3. In runs 8–14, runs 1 to 7 were substantially repeated substituting HZSM-11 for HZSM-5 zeolite catalyst. Note should be taken that within the temperature range of 300° to 400° C, the isobutane to normal butane ratio was consistently over 6 and even at the higher reported temperatures was higher than with HZSM-5.

Runs 15, 16, and 17 are included to substantiate the allegations of unexpected superiority of results with respect to ZSM-11 catalyzed conversions over a range of operating conditions.

TABLE I

| | REACTION PRODUCTS FROM ETHYLENE DILUTED WITH NITROGEN OVER HZSM-5 | | | | | | |
|---|---|---|---|---|---|---|---|
| RUN NO. | 1 | 2 | 3 | 4* | 5 | 6 | 7 |
| REACTANTS | $C_2H_4$ $N_2$ | $C_2H_4$ $N_2$ | $C_2H_4$ $N_2$ | $C_2H_4$ $N_2$ | $C_2H_4$ $N_2$ | $C_2H_4$ $N_2$ | $C_2H_4$ $N_2$ |
| TEMPERATURE ° C | 300 | 350 | 400 | 450 | 500 | 550 | 600 |
| WHSV (C.T.SEC.) | 1.5 | 1.5 | 1.5 | 1.5 | 1.5 | 1.5 | 1.5 |
| ALIPHATICS | | | | | | | |
| $H_2$ | .039 | .062 | .115 | .249 | .437 | .762 | 1.354 |
| CO | 0 | 0 | 0 | 0 | 0 | 0 | 0 |
| $CO_2$ | 0 | 0 | 0 | 0 | 0 | 0 | 0 |
| $CH_4$ | 0 | 0 | .076 | .395 | .926 | 2.55 | 4.98 |
| $C_2H_6$ | .9 | 1.0 | 1.0 | 1.8 | 3.5 | 7.2 | 11.5 |
| $C_2H_4$ | 21.3 | 2.5 | 1.2 | 3.2 | 5.4 | 12.0 | 19.1 |
| $C_3H_8$ | 5.3 | 11.4 | 14.6 | 19.2 | 20.4 | 15.1 | 8.0 |
| $C_3H_6$ | 2.3 | 1.9 | 1.1 | 3.5 | 9.1 | 14.4 | 12.9 |
| i-$C_4H_{10}$ | 6.8 | 8.9 | 13.2 | 12.5 | 9.1 | 2.4 | .2 |
| n-$C_4H_{10}$ | 3.0 | 3.8 | 5.7 | 6.3 | 4.6 | 2.0 | .7 |
| $C_4H_8$ | 5.0 | 4.1 | 2.7 | 4.2 | 4.7 | 3.6 | 1.4 |
| $C_4H_6$ | 3.9 | 4.7 | 3.5 | 3.6 | 2.6 | 1.6 | .3 |
| $C_5$ | 16.7 | 21.9 | 14.0 | 8.5 | 6.5 | 4.5 | 4.7 |
| $C_6$ | 11.7 | 13.7 | 7.1 | 2.3 | 1.1 | .2 | .1 |

TABLE I-continued

REACTION PRODUCTS FROM ETHYLENE DILUTED WITH NITROGEN OVER HZSM-5

| RUN NO. | 1 | 2 | 3 | 4* | 5 | 6 | 7 |
|---|---|---|---|---|---|---|---|
| REACTANTS | $C_2H_4$ $N_2$ | $C_2H_4$ $N_2$ | $C_2H_4$ $N_2$ | $C_2H_4$ $N_2$ | $C_2H_4$ $N_2$ | $C_2H_4$ $N_2$ | $C_2H_4$ $N_2$ |
| TEMPERATURE °C | 300 | 350 | 400 | 450 | 500 | 550 | 600 |
| WHSV (C.T.SEC.) | 1.5 | 1.5 | 1.5 | 1.5 | 1.5 | 1.5 | 1.5 |
| $C_7+$ | 5.1 | 4.5 | 3.0 | 1.3 | .9 | .6 | .6 |
| BENZENE | .7 | .8 | 1.1 | 2.3 | 3.4 | 5.1 | 7.5 |
| TOLUENE | 3.2 | 4.0 | 7.2 | 11.1 | 12.3 | 14.4 | 14.7 |
| $ArC_8$ | 5.5 | 6.8 | 10.7 | 12.4 | 12.4 | 10.7 | 8.1 |
| $ArC_9$ | 5.7 | 6.4 | 7.6 | 4.6 | 3.0 | 1.8 | 1.2 |
| $ArC_{10}+$ | 3.0 | 3.6 | 6.0 | 2.5 | 1.2 | 1.1 | 2.5 |
| TOTAL AROM. | 18.1 | 21.6 | 32.6 | 32.9 | 32.2 | 33.1 | 34.1 |
| ALIPH. | 81.9 | 78.4 | 67.3 | 66.9 | 67.3 | 66.2 | 64.5 |
| CONVERSION | 80.4 | 97.5 | 98.8 | 96.8 | 94.6 | 88.4 | 92.3 |
| MAT. BAL. | 91.8 | 96.9 | 98.7 | 100.1 | 98.7 | 96.7 | 92.5 |

*CATALYST REGENERATED IN AIR, OVERNIGHT

TABLE II

REACTION PRODUCTS FROM ETHYLENE DILUTED WITH NITROGEN, OVER HZSM-11

| RUN NO. | 8 | 9 | 10 | 11 | 12 | 13 | 14 |
|---|---|---|---|---|---|---|---|
| REACTANTS | $C_2H_4$ $N_2$ | $C_2H_4$ $N_2$ | $C_2H_4$ $N_2$ | $C_2H_4$ $N_2$ | $C_2H_4$ $N_2$ | $C_2H_4$ $N_2$ | $C_2H_4$ $N_2$ |
| TEMPERATURE °C | 300 | 350 | 400 | 450 | 500 | 550 | 600 |
| WHSV (C.T. SEC.) | 1.5 | 1.5 | 1.5 | 1.5 | 1.5 | 1.5 | 1.5 |
| ALIPHATICS | | | | | | | |
| $H_2$ | .053 | .065 | .105 | .213 | .327 | .484 | .730 |
| CO | 0 | 0 | 0 | 0 | 0 | 0 | 0 |
| $CO_2$ | 0 | 0 | 0 | 0 | 0 | 0 | 0 |
| $CH_4$ | 0 | 0 | .061 | .217 | .615 | 1.6 | 3.5 |
| $C_2H_6$ | .4 | .4 | .8 | 1.5 | 2.5 | 5.0 | 8.9 |
| $C_2H_4$ | 24.4 | 4.6 | 1.5 | 1.3 | 4.7 | 11.1 | 17.3 |
| $C_3H_8$ | 4.4 | 7.3 | 13.5 | 15.8 | 18.1 | 15.4 | 9.2 |
| $C_3H_6$ | 3.1 | 1.1 | 1.0 | 2.7 | 8.6 | 15.6 | 16.6 |
| $i-C_4H_{10}$ | 8.8 | 13.5 | 16.5 | 11.7 | 9.5 | 5.0 | 1.4 |
| $n-C_4H_{10}$ | .6 | 1.4 | 1.7 | 5.3 | 5.1 | 3.5 | 1.4 |
| $C_4H_8$ | 5.8 | 4.3 | 2.4 | 3.6 | 5.0 | 4.8 | 5.2 |
| $C_4H_6$ | 2.8 | 3.9 | 2.7 | 3.0 | 3.1 | 2.6 | 1.2 |
| $C_5$ | 16.2 | 17.2 | 13.0 | 11.2 | 7.1 | 5.7 | 4.1 |
| $C_6$ | 9.9 | 12.8 | 5.9 | 4.3 | 2.1 | .6 | .3 |
| $C_7+$ | 4.8 | 4.7 | 2.5 | 2.1 | 1.3 | .5 | .4 |
| BENZENE | .3 | .4 | 1.0 | 1.8 | 2.4 | 2.7 | 4.4 |
| TOLUENE | 2.8 | 4.1 | 5.5 | 10.7 | 10.6 | 10.7 | 13.0 |
| $ArC_8$ | 4.9 | 8.0 | 15.6 | 12.9 | 11.9 | 10.3 | 9.1 |
| $ArC_9$ | 7.1 | 11.5 | 11.8 | 7.5 | 4.4 | 2.5 | 1.7 |
| $ArC_{10}+$ | 3.6 | 4.6 | 4.9 | 4.2 | 2.6 | 1.8 | 1.5 |
| TOTAL AROM. | 18.7 | 28.7 | 38.4 | 37.0 | 31.9 | 28.0 | 29.8 |
| ALIPH. | 81.2 | 71.2 | 61.5 | 62.7 | 67.7 | 71.5 | 69.5 |
| CONVERSION | 78.9 | 94.8 | 98.4 | 98.7 | 95.3 | 88.7 | 82.4 |
| MAT. BAL. | 86.3 | 112.2 | 103.2 | 99.6 | 99.3 | 101.4 | 101 |

TABLE III

REACTION PRODUCTS FROM ETHYLENE WITHOUT DILUENT OVER HZSM-11

| RUN NO. | 15 | 16 | 17 |
|---|---|---|---|
| REACTANTS | $C_2H_4$ | $C_2H_4$ | $C_2H_4$ |
| TEMPERATURE °C | 395 | 460 | 515 |
| WHSV (C.T. SEC.) | 3.1 | 6.1 | 9.2 |
| ALIPHATICS | | | |
| $H_2$ | 0 | .02 | .2 |
| CO | 0 | 0 | 0 |
| $CO_2$ | 0 | 0 | 0 |
| $CH_4$ | .2 | .2 | .5 |
| $C_2H_6$ | 1.6 | 2.4 | 5.3 |
| $C_2H_4$ | 2.6 | 2.2 | 11.4 |
| $C_3H_8$ | 15.1 | 17.7 | 15.8 |
| $C_3H_6$ | 3.1 | 2.3 | 10.9 |
| $i-C_4H_{10}$ | 15.6 | 13.1 | 6.0 |
| $n-C_4H_{10}$ | 2.0 | 2.1 | .5 |
| $C_4H_8$ | 4.3 | 2.6 | 6.2 |
| $C_4H_6$ | 3.3 | 4.3 | .6 |
| $C_5$ | 17.2 | 12.0 | 11.6 |
| $C_6$ | 6.9 | 3.9 | 3.6 |
| $C_7+$ | 0 | 0 | .2 |
| BENZENE | .9 | .5 | .3 |
| TOLUENE | 2.6 | 6.0 | 6.5 |
| $ArC_8$ | 9.6 | 15.6 | 13.3 |
| $ArC_9$ | 9.8 | 9.7 | 5.4 |
| $ArC_{10}+$ | 5.3 | 5.4 | 1.7 |
| TOTAL AROM. | 28.2 | 37.2 | 27.1 |
| ALIPH. | 71.8 | 62.8 | 72.7 |
| CONVERSION | 97.5 | 97.8 | 88.4 |
| MAT. BAL. | 94.7 | 103.2 | 101.7 |

We claim:

1. In the process of converting a feed consisting of ethylene to a product comprising isobutane and n-butane by contacting such ethylene with a ZSM-5 type of crystalline alumino-silicate zeolite at a given set of operating conditions including a space velocity of about 0.5 to 10 WHSV and a temperature of at least about 300° C; the improvement which comprises utilizing as said zeolite ZSM-11 and operating at said given combination set of conditions such as to produce a product having an iso-butane to n-butane ratio of at least about 6 and separating a $C_4$ fraction comprising butanes that contain at least about 85% iso-butane.

2. The improved process claimed in claim 1 carried out with undiluted ethylene feed up to about 515° C.

3. The improved process claimed in claim 1 carried out with an inert gas diluted ethylene feed up to about 400° C.

4. The improved process claimed in claim 1 carried out using HZSM-11 as the zeolite.